Figure 1:
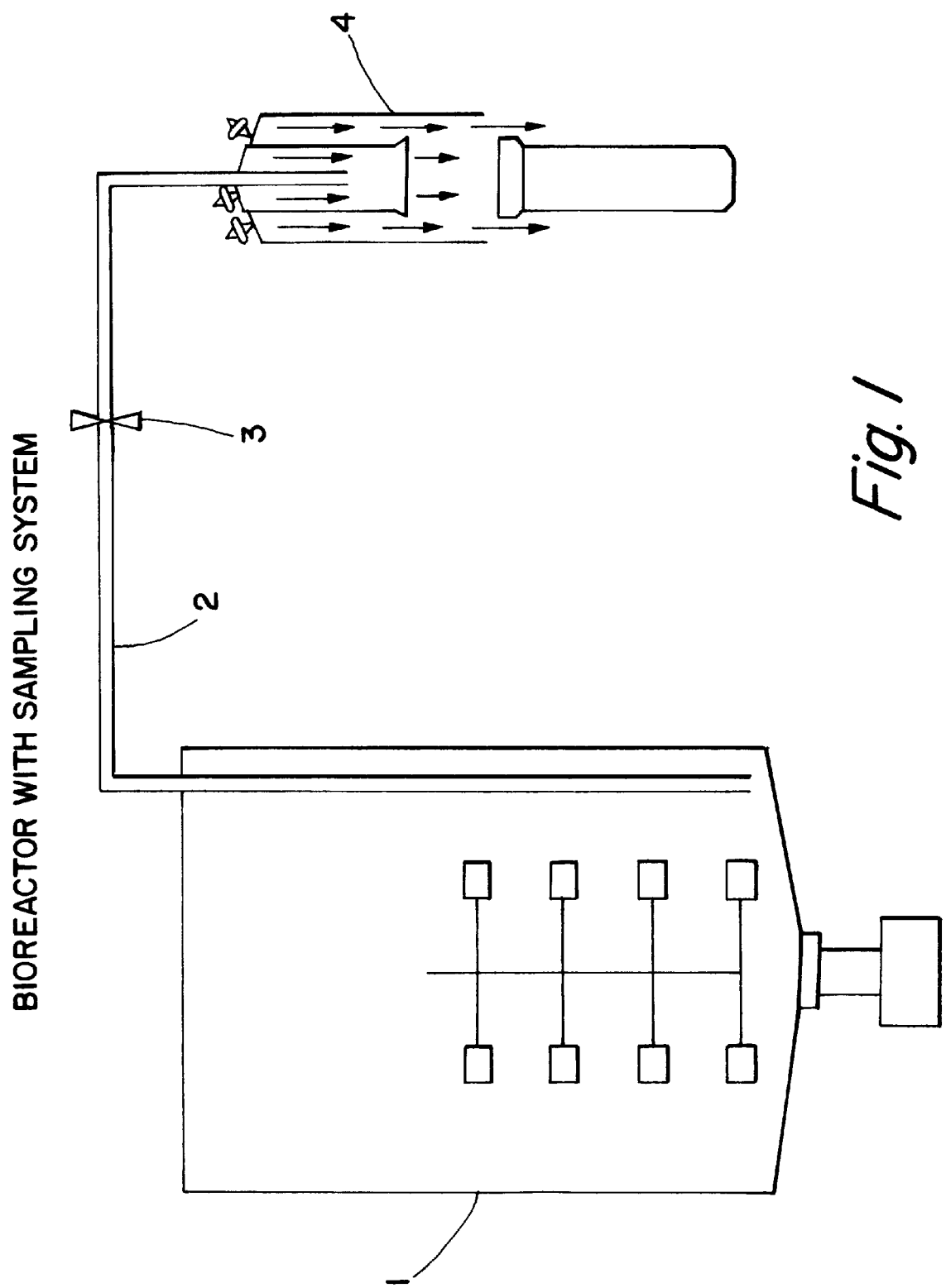

United States Patent [19]
Schorn et al.

[11] Patent Number: 6,085,602
[45] Date of Patent: Jul. 11, 2000

[54] SAMPLING SYSTEM FOR USE IN THE ANALYSIS OF BIOLOGICAL PROCESSES

[75] Inventors: Peter Schorn, Langenau; Hans Voigt; Wolfgang Noe, both of Biberach, all of Germany

[73] Assignee: Dr. Karl Thomae GmbH, Biberach, Germany

[21] Appl. No.: 08/776,795

[22] PCT Filed: Sep. 12, 1995

[86] PCT No.: PCT/EP95/03587

§ 371 Date: Jun. 3, 1997

§ 102(e) Date: Jun. 3, 1997

[87] PCT Pub. No.: WO96/08556

PCT Pub. Date: Mar. 21, 1996

[30] Foreign Application Priority Data

Sep. 13, 1994 [DE] Germany .............................. 44 32 599

[51] Int. Cl.[7] ...................................................... G01N 1/00
[52] U.S. Cl. .......................................................... 73/863.83
[58] Field of Search ........................... 73/863.31, 863.81, 73/863.83, 863.86; 141/97; 435/309.1, 309.2

[56] References Cited

U.S. PATENT DOCUMENTS

| | | | |
|---|---|---|---|
| 4,669,321 | 6/1987 | Meyer | 73/863.85 |
| 5,296,197 | 3/1994 | Newberg et al. | 73/863.86 |
| 5,370,146 | 12/1994 | King et al. | 73/863.86 |

*Primary Examiner*—Robert Raevis
*Attorney, Agent, or Firm*—Robert P. Raymond; Alan R. Stempel; Mary-Ellen M. Devlin

[57] ABSTRACT

The invention relates to a sampling device, in which the site of separation from the microbiologically contaminated environment is constructed as a sterile protective gas current according to the laminar air-flow principle under a housing bell (7), the site of connection of the inner tube (11) to the sample tube (10) being so designed that it occurs inside to just below the housing bell (7), fixedly or with no fixed connection, and for automatic operation occurs just below the housing bell (7), with no fixed connection.

2 Claims, 2 Drawing Sheets

BIOREACTOR WITH SAMPLING SYSTEM

SAMPLING DEVICE

SAMPLING SYSTEM FOR USE IN THE ANALYSIS OF BIOLOGICAL PROCESSES

The present invention relates to a new sampling device which makes it possible to carry out sterile removal of cell culture samples and other liquid media from bioreactors or sterile containers, protection from recontamination being provided by means of a sterile-filtered inert gas current.

The optimising of biotechnologically relevant production methods depends primarily on progress in the field of bioprocessing analysis, since this can provide findings which may lead to improved process control. Increasingly, modern methods of analysis such as cytofluorometry, high pressure liquid chromatography and biosensors are used for this. The prerequisite for this is the use of suitable sampling systems which constitute the link with the contents of the fermenter.

In the cultivation of animal, bacterial and plant cells, the aseptic method of operation and the sterile equipment used in the fermentation are of particular importance, since samples have to be taken continuously throughout the fermentation process in order to determine important parameters such as the growth characterisitics of the culture, the magnitudes relating to cell status and metabolic values.

The actual sampling from the bioreactor constitutes a critical operation, since it breaks through the sterile barrier to the contents of the fermenter. Therefore, in the case of fermentations lasting several weeks or in the event of a high sampling frequency, simple and reliable sampling methods are of great importance to the success of the process.

Moreover, sampling must give a true representation of the fermenter contents and must always be available, whilst the use of automated analytical systems increasingly demands the possibility of fully automated sampling.

The sampling devices used hitherto for this purpose are either provided by the manufacturers of bioreactors or are designs produced by the users themselves. These often improvised aids can only partly satisfy the abovementioned requirements or have the following specific disadvantages:

An important design feature is the manner of preventing back-contamination of the fermenter contents through the sampling route, since this constitutes the site of opening to the microbiologically contaminated environment.

This problem is solved in various ways:

By piercing septa or membranes on presterilised sample vials. This method is used frequently, especially in bacterial fermentation. However, this method is complicated and not very reliable to operate, and also requires chemical or thermal disinfection of the piercing needle, e.g. by means of a flame.

By disinfection of a sampling route using chemical agents such as ethanol. This method brings the risk of sample falsification, undesirable chemical attack and high-risk reattachment of the sample vessel.

By using sealed sampling systems with vials or disposable syringes. In this case, a sampling route is used only once and then abandoned. This method therefore requires dimensionally large constructions and frequent changing of the vessel arrangements, and also produces large amounts of material for disposal, e.g. syringes.

By thermal disinfection of the opening, e.g. with steam. This method requires pressuretight joints such as, for example, suitable tubing and considerable time spent on cooling, and is thus not suitable for laboratory reactors, in particular.

By using membranes which are impermeable to bacteria. This method is used particularly for the method of analysis known as FIA (Flow Injection Analysis). However, with this method, only cell-free sampling is possible.

Generally speaking, the above methods (apart from the FIA system) are unsuitable for automation owing to the need for manual operation and are thus not universally usable.

Commercially obtainable systems are described, for example, in Biotech-Forum 6, 274–288 (1989) and marketed by the firm Bioengineering, CH 8636 Wald.

The aim of the present invention is therefore to find a sampling system which satisfies the following minimum requirements:

compact construction, ease of assembly
universally usable for sterile sampling
reliable mode of operation
no contamination of the sample material by chemical agents
ease of handling and constant accessibility
no accumulation of used materials such as disinfectants, syringes, etc.
no limitation to frequency of sampling
fully automatable system, e.g. possibility of attachment to autosampler for online analysis According to the invention, the aim is achieved by the fact that, in the sampling device according to the invention, the point of separation from the microbiologically contaminated environment is constructed as a sterile defined protective gas current, which preferably consists of sterile air, according to the laminar air flow principle, in such a way that a laminar protective gas current (cf. for example Kohlbausch in Praktische Physik, page 138, vol. 1, published by Teubner, Stuttgart, 1968) is advantageously passed through the sampling device from above, said device comprising at least one, but preferably two concentrically mounted tubes, the space between the outer and inner tubes defining the protective hood for the sterile gas flow and the connection site of the inner tube (11) to the sample tube (10) being such that it occurs inside to just below the housing bell (7), fixedly or without any fixed connection, and, for automatic operation, it occurs just below the housing bell (7) without any fixed connection.

In a preferred sampling device the sampling housing (7) preferably consists of two concentrically mounted tubes, fixed together at the top, preferably made of glass. A thin tube (11), preferably also of glass, is passed through the common central line of this double housing, for transporting the sample liquid. The entire housing bell may be permanently supplied with a turbulence-free and sterile-filtered protective gas or gas, preferably sterile-filtered air, through the air filter openings (9) shown, whilst preferably a laminar gas current of this kind is produced by passing the gas through a permeable membrane (8) arranged above the end of the inner tube (11), and flows out again at the open lower end of the housing. This gas current displaces the microbiologically contaminated ambient air from a specific flow rate onward and itself constitutes a protection of the sampling site from recontamination. The flow rate is conveniently in the range from 0.1 to 2 m/sec., but preferably between 0.4 and 0.6 m/sec., as used for example in safety workbenches for producing a laminar, low-turbulence air current.

The sampling process itself, i.e. the transferring of the sterile liquid, has the following possibilities, which demonstrate the great versatility of the device:

(A) Fixed Attachment of the Sample Vessel by Hand

The sterile sample tube is inserted in the housing bell (7) from below and connected to the mating thread or quick-fit closure provided on the inner housing tube. In this case, the container to be filled is ventilated through the air filter (9.1).

(B) Transferring the Sample by Hand with No Fixed Attachment

The upper edge of the sample vessel is held inside the housing bell (7) directly below the inner tube (11), i.e. underneath the sample outlet.

(C) Automatic Filling of Sample Tubes with No Fixed Attachment

In this mode of operation, a number of sample vessels are placed in a rotating sample carousel (Autosampler), for example, and automatically positioned directly below the housing bell (7).

Figure 2:
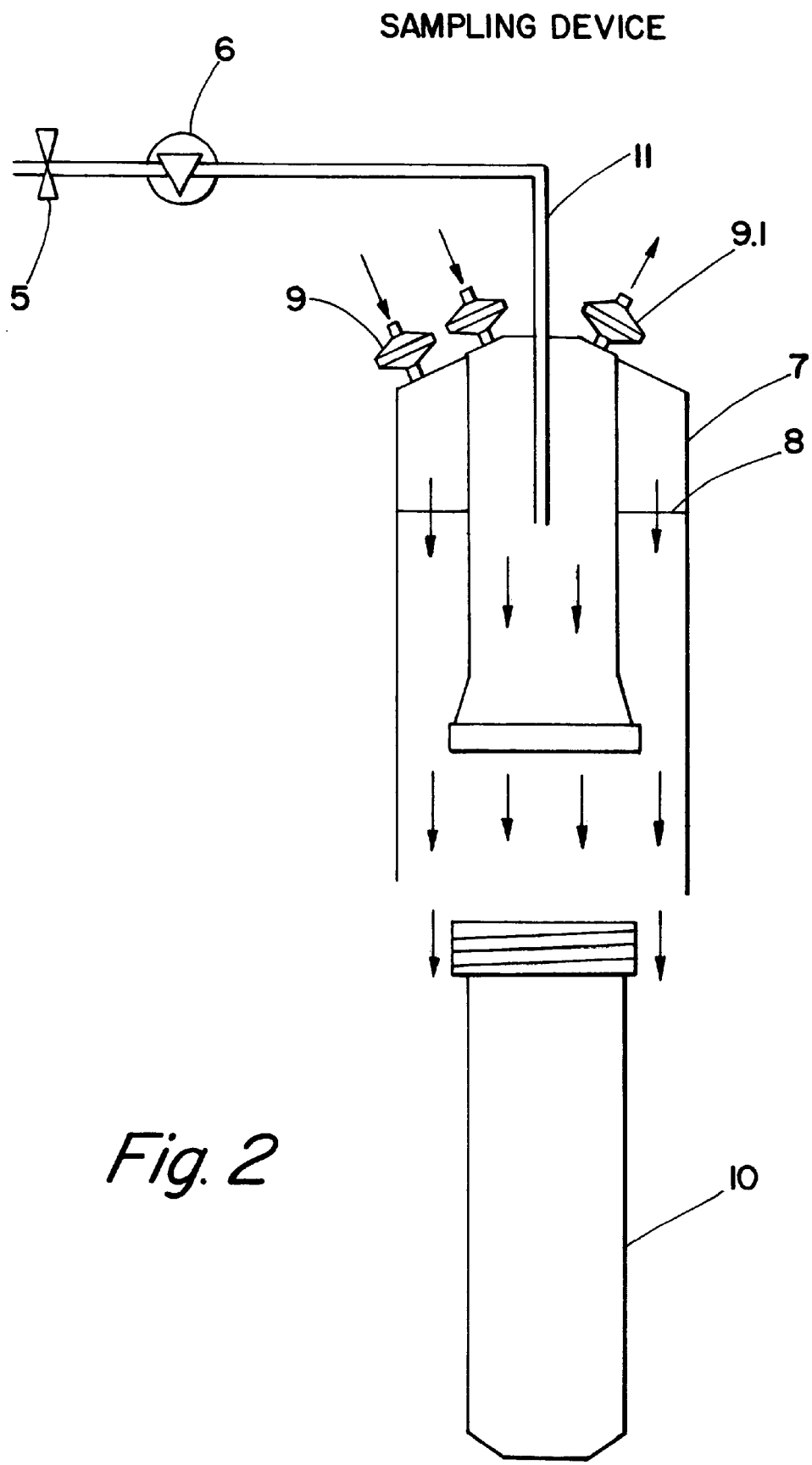

FIGS. 1 and 2 illustrate a preferred embodiment of the sampling device according to the invention:

FIG. 1 diagrammatically shows the entire function of the device in conjunction with the bioreactor.

A) Sterilisation of the Device

The sampling device is connected to the outlet of the immersion sampling tube of the fermenter (1) via a suitable connection (3) and a hose, preferably of silicone, and autoclaved together with the fermenter. To do this, the hood (7) must be sealed off at the bottom end by means of a suitable cover. The opening (3) is preferably a standard commercial quick-release coupling for sterile-technical joints, e.g. as made by Swagelock of the USA, which allows replacement or subsequent adding on of the sterilised device if necessary.

B) Mode of Operation

After sterilisation, an inert protective gas, preferably sterile compressed air, as is available in any laboratory, is applied to the or each, preferably two, protective gas inlet openings (9), which are preferably air filters (e.g. Acrodisc, 0.2 μm pore width, made by Gelman). At the same time or, better still, before the removal of the cover used for the sterilisation, the preliminary pressure of the gas is adjusted so as to achieve a gas velocity of about 0.5 m/s. This set-up is maintained throughout the entire process and permits constant access to the fermenter contents.

FIG. 2 shows the sampling device in outline:

The housing (7) consists of two concentrically mounted tubes which are preferably made from heat-resistant glass, the space between the outer and inner tubes forming the protective hood for sterile gassing. In this particular instance, the external dimension of the housing is 10 cm long and 4 cm in diameter; however, other dimensions are also possible. Into the inner housing part, which may if necessary be fitted with one or more ventilating valves (9.1), appropriately produced in the same operation as the protective gas inlet openings, is inserted a tube (11), e.g. a glass tube, which is connected to the bioreactor (1) via a connection, e.g. a silicone hose connection, and via a quick-release coupling (5). A peristaltic pump (6), which is conveniently located between the quick-release coupling (5) and the sampling device, delivers the desired volume of sample directly into a suitable sample vessel (10). The cell culture liquid is protected from foreign contamination by a gas current which is passed through the air filters (9) described above. It is beneficial if a permeable membrane (8), e.g. of polyvinyldifluoride or a suitable glass frit, is placed in the gap between the outer and inner tubes of the protective hood (7) to ensure uniform gas distribution and a laminar gas flow. The laminar flow coming out displaces the ambient air and reliably prevents infection of the sample liquid.

Surprisingly, a small housing volume of the protective hood (7) is sufficient to ensure reliable operation of the device. In the example described, the outer housing volume is only about 110 cm$^3$. This enables the device to be compact in construction.

In manual sampling, a pre-sterilised sample vessel (10), ideally a 15 ml test tube, e.g. made by Falcon, is screwed onto the inner housing ring of the inner tube, although other types of connection such as snap-fit closures may be considered, or is simply held under the glass tube (11), appropriately inside the hood (7). In the case of a fixed connection, ventilation is preferably effected through the filter unit (9.1), which is usefully integrally formed with the device.

In automatic sampling the sample vessel (10) is positioned as shown and filled automatically by actuation of the pump (6). The sample vessel is arranged underneath the hood (7) at a spacing of 1 to 50 mm, but preferably 5 to 20 mm, so as to enable the sample tube to be filled automatically.

In any case, before each measuring cycle, in order to obtain a representative sample, a specific volume of first runnings, corresponding to the contents of the silicone hose up to the fermenter, must be discarded.

According to the invention, the new sampling device is thus characterised by the following features:

it has no mechanically moving parts it preferably uses pathogen-free filtered compressed air or another gas as the sole medium for sterile operation, after the device has first been thermally inactivated a constant, defined gas flow underneath the bell described above permits open handling of the presterilised sample vessel, i.e. direct contact with the sampling device itself is not absolutely necessary samples can be taken at any time with no preparation and with no waste of time.

We claim:

1. A sampling system, for withdrawing a sample of liquid contained within a vessel and conveying it into a sample tube under sterile conditions, the system comprising:

(a) a conduit having a first end and a second end which extends through a wall of the vessel so that the first end of the conduit is within the vessel, for withdrawing liquid from the vessel;

(b) a pump for causing liquid to flow from the vessel, through the conduit, from the first end toward the second end thereof, so that the liquid is discharged from the second end of the conduit;

(c) a housing bell comprising:

(1) an outer tube having a first end, which is closed, and a second end, which is open, and (2) a second tube having a first end, which is closed and a second end, which is open, the second tube being disposed within the outer tube, arranged concentrically about a common axis, with the first (closed) end of the second tube being fixed to the first (closed) end of the outer tube, a terminal portion of the conduit passing through the closed ends of the outer and second tubes and extending within the second tube along the common axis, the space within the outer tube constituting a protective hood, the second (open) end of the second tube being located between the first and second ends of the outer tube within the protective hood, the second end of the conduit being located between the first and second ends of the second tube, the open end of the outer tube being configured to accept entry of the mouth of a sample tube into the protective hood so that, when a sample tube is so positioned, liquid flowing out of the second end of the conduit is deposited into the sample tube, the second end of the second tube having means by which it may be detachably coupled to the mouth of a sample tube placed within the protective hood; and, (d) means for introducing sterile gas, under pressure, through the closed ends of the outer and second tubes, into the protective hood, to thereby produce laminar flows of sterile gas which displace ambient air from within the protective hood.

2. A sampling system, for withdrawing a sample of liquid contained within a vessel and conveying it into a sample tube under sterile conditions, the system comprising:

(a) a conduit having a first end and a second end which extends through a wall of the vessel so that the first end of the conduit is within the vessel, for withdrawing liquid from the vessel;

(b) a pump for causing liquid to flow from the vessel, through the conduit, from the first end toward the second end thereof, so that the liquid is discharged from the second end of the conduit;

(c) a housing bell comprising:
   (i) an outer tube having a first end, which is closed, and a second end, which is open, a terminal portion of the conduit passing through the closed end of the outer tube and extending along a common axis so that the outer tube and the terminal portion of the conduit are concentrically arranged about the common axis, the space within the outer tube constituting a protective hood, the second end of the conduit being located between the first and second ends of the outer tube within the protective hood, the open end of the outer tube being configured to accept entry of the mouth of a sample tube into the protective hood so that, when a sample tube is so positioned, liquid flowing out of the second end of the conduit is deposited into the sample tube; and,
   (ii) an inner tube having a first end, which is closed, and a second end, which is open, the inner tube being concentrically arranged about the common axis, between the outer tube and the terminal portion of the conduit, within the protective hood, the first (closed) end of the inner tube being fixed to the first, (closed) end of the outer tube and the second (open) end of the inner tube being located between the first and second ends of the outer tube, the second end of the inner tube having means by which it may be detachably coupled to the mouth of a sample tube placed within the protective hood;

(d) means for introducing sterile gas, under pressure, through the closed end of the outer tube into the protective hood, to thereby produce a laminar flow of sterile gas which displaces ambient air from within the protective hood; and, (e) means for introducing sterile gas, under pressure, into the inner tube, to thereby produce a laminar flow of sterile gas which displaces ambient air from within the inner tube.

* * * * *